(12) United States Patent
Mäntele et al.

(10) Patent No.: US 7,920,260 B2
(45) Date of Patent: Apr. 5, 2011

(54) MEASURING DEVICE FOR DETERMINING THE SIZE, SIZE DISTRIBUTION AND QUANTITY OF PARTICLES IN THE NANOSCOPIC RANGE

(75) Inventors: Werner Mäntele, Blakenbach (DE); Vitali Vogel, Frankfurt (DE); Oliver Klein, Friedberg (DE); Lea Schröder, Aachen (DE)

(73) Assignee: Johann Wolfgang Goethe-Universität, Frankfurt am Main (DE)

( * ) Notice: Subject to any disclaimer, the term of this patent is extended or adjusted under 35 U.S.C. 154(b) by 182 days.

(21) Appl. No.: 12/278,573

(22) PCT Filed: Feb. 2, 2007

(86) PCT No.: PCT/DE2007/000218
§ 371 (c)(1),
(2), (4) Date: Dec. 16, 2008

(87) PCT Pub. No.: WO2007/090378
PCT Pub. Date: Aug. 16, 2007

(65) Prior Publication Data
US 2009/0185160 A1 Jul. 23, 2009

(30) Foreign Application Priority Data

Feb. 6, 2006 (DE) .......................... 10 2006 005 574

(51) Int. Cl.
*G01N 15/02* (2006.01)
*G01N 21/00* (2006.01)
(52) U.S. Cl. ........................................ 356/336; 356/340
(58) Field of Classification Search ..... 356/237.1–237.5
See application file for complete search history.

(56) References Cited

U.S. PATENT DOCUMENTS 4,676,641 A * 6/1987 Bott ............................. 356/336
(Continued)

FOREIGN PATENT DOCUMENTS

CA 2 507 876 A1 6/2004
(Continued)

OTHER PUBLICATIONS

Cumming, A.M., et al., "In Vitro Neutralization of Heparin in Plasma Prior to the Activated Partial Thromboplastin Time Test: An Assessment of Four Heparin Antagonists and Two Anion Exchange Resins," Thrombosis Research 41(1):43-56, Jan. 1986.

(Continued)

*Primary Examiner* — Gregory J Toatley
*Assistant Examiner* — Jarreas C. Underwood
(74) *Attorney, Agent, or Firm* — Christensen O'Connor Johnson Kindness PLLC

(57) ABSTRACT

A measuring device determines the size, size distribution, and/or concentration of nanoscopic particles or hollow spaces in a measuring sample, the degree of opacity of such measuring samples, or the degree of roughness of surfaces by determining the wavelength and scattering angle dependent intensities of a measuring radiation scattered on a measuring sample. The measuring device comprises a retaining device for a measuring sample to be measured, a detector comprising at least one detector inlet, an evaluation unit, and at least two radiation sources that are respectively at a distance from each other and at a distance from the measuring sample. Via the radiation sources, a ray bundle can in each case be emitted in an essentially parallel beam in the direction of the measuring sample. The ray bundles directed onto the measuring sample are aligned or can be aligned in different angles onto the measuring sample.

46 Claims, 1 Drawing Sheet

U.S. PATENT DOCUMENTS

| | | | |
|---|---|---|---|
| 4,917,495 A * | 4/1990 | Steenhoek | 356/328 |
| 5,416,580 A * | 5/1995 | Trainer | 356/336 |
| 5,619,324 A | 4/1997 | Harvill | |
| 5,739,911 A | 4/1998 | Holzapfel | |
| 5,808,738 A | 9/1998 | Garcia-Rubio | |
| 6,118,531 A * | 9/2000 | Hertel et al. | 356/336 |
| 6,137,572 A | 10/2000 | DeFreez | |
| 7,245,364 B2 * | 7/2007 | Moriya | 356/237.1 |
| 2001/0052975 A1 | 12/2001 | Biellak | |
| 2002/0180972 A1 * | 12/2002 | Ansari et al. | 356/336 |

FOREIGN PATENT DOCUMENTS

| | | |
|---|---|---|
| DE | 44 14 166 C1 | 12/1995 |
| DE | 195 10 034 A1 | 9/1996 |
| DE | 195 25 874 A1 | 1/1997 |
| DE | 197 24 228 A1 | 12/1998 |
| DE | 696 00 969 T2 | 6/1999 |
| DE | 199 54 702 A1 | 5/2001 |
| EP | 1 221 620 A2 | 7/2002 |
| WO | 01/20304 A2 | 3/2001 |
| WO | 01/36937 A1 | 5/2001 |
| WO | 03/062800 A2 | 7/2003 |
| WO | 2004/051205 A2 | 6/2004 |

OTHER PUBLICATIONS

International Search Report dated Aug. 10, 2007, issued in corresponding International Application No. PCT/DE2007/000218, filed Feb. 2, 2007.

Mignani, A.G., et al., "Scattered Colorimetry and Multivariate Data Processing as an Objective Tool for Liquid Mapping," Proceedings of the 17th International Conference on Optical Fibre Sensors, International Society for Optical Engineering (SPIE), Bruges, Belgium, May 23, 2005, vol. 5855, pp. 38-41.

Mignani, A.G., et al., "Spectral Nephelometry for the Geographic Classification of Italian Extra Virgin Olive Oils," Sensors and Actuators B: Chemical 111-112:363-369, Nov. 2005.

* cited by examiner

MEASURING DEVICE FOR DETERMINING THE SIZE, SIZE DISTRIBUTION AND QUANTITY OF PARTICLES IN THE NANOSCOPIC RANGE

CROSS-REFERENCES TO RELATED APPLICATIONS

This application is a 371 national stage of PCT Application No. PCT/DE2007/000218, filed Feb. 2, 2007, which claims the benefit of German Patent Application No. DE 10 2006 005 0574.8-52, filed Feb. 6, 2006, the disclosures of which are incorporated by reference herein in their entirety.

FIELD

The present application relates to a measuring device and to a method for determining the size, size distribution and/or the quantity of nanoscopic particles or hollow spaces in a measuring sample, the degree of opacity of such measuring samples or the degree of roughness of surfaces of solid bodies using scattered light. Furthermore, the application relates to the determination of heparin, in particular in heparinized blood or blood serum samples, using scattered light.

BACKGROUND

Visual methods for determining the size of particles have already been used in a very wide variety of ways. The light scattering plays a minor role in these methods. Here, the Rayleigh, Mie, Debye, Rayleigh-Gans, and Fraunhofer theories of scattering are used. While the Rayleigh theory of scattering can only be applied for particle sizes smaller than approximately $1/10$ of the wavelength of the light which falls, and only implies one single scattering center, the Mie theory of scattering can be applied to particle sizes in the range of 0.1 to 10 times the measured wavelength. However, the Mie theory is highly complex and requires a powerful computer. The Debye, Rayleigh, Gans, and Fraunhofer theories of scattering are by contrast based on simple assumptions, and are accordingly less complex; however, they are usually only suitable for determining larger particles.

According to a first embodiment of known measuring devices for determining the size of particles in the nanoscopic range using light scattering, use is made of a light source of monochromatic light, i.e., laser light, and a plurality of detectors, which are attached at different angles to the sample bodies to be measured. A device of this type is described, e.g., in DE 696 00 969 T2. Here, a compound laser deflection instrument is used, with which individual scattering signals can be systematically generated. The method described in this document enables the measurement of particle size distributions via light scattering.

In a similar manner, in DE 197 24 228 A1, particle size distributions and concentrations of particles can be determined with the aid of electrically modulated light sources by detecting the scattered radiation under different scattering angles. For a fixed individual wavelength, the scattering angle is successively set by rotating a minor, and the respective scattered light portion is detected.

According to a second embodiment of known measuring devices to determine particle sizes or particle size distributions with the aid of a light source of monochromatic light, use is made not of individual, fixed position detectors, but of a field of a plurality of detectors. For example, according to the measuring device disclosed in DE 195 10 034 A1, a laser beam which is scattered on a dispersed particle sample is depicted by means of a field of photodetectors which are arranged at the burning level of the depiction device, and fed to an evaluation measuring device. The measuring device found is designed to enable the most compact and visually stable construction possible. Furthermore, the diameter of the measuring beam is designed to be variably adaptable to the demands of the respective measuring range, so that extended particle collectives can also be determined down to the finest particles with regard to their size distribution.

A third embodiment of known measuring devices for determining the particle size or particle size distribution using light scattering can be found in U.S. Pat. No. 6,137,572, in which by means of the dynamic light scattering which uses the double broadening of the scattered light against the narrow strip of the laser light which is beamed in, the sensitivity for the determination of the particle size is significantly increased again.

Finally, particle sizes or particle densities can also be determined according to a further embodiment of a measuring device known from the prior art by means of interference measurements, such as those disclosed, e.g., in DE 199 54 702 A1 and DE 195 25 847 A1. With the methods described in these documents, an interference image is generated with coherent light of a laser, following which the desired information on particle density and size can be estimated from the interference pattern received. Thus, for example, the device according to DE 195 25 847 A1 is equipped with a deflection unit which permits a change of direction of the illuminating laser beam in such a manner that during measurement, said laser beam is guided into an angle range around the particle to be measured.

The optical methods used to date to determine particle size or particle size distributions require expensive apparatus and also do not permit, or do not automatically permit, time-dispersed measurements.

It would therefore be desirable to be able to draw on measuring devices to determine the size of particles in the nanoscopic range using scattered radiation which are not encumbered by the disadvantages of the prior art.

SUMMARY AND INITIAL DESCRIPTION

For at least the above reasons, an object of the present application is to provide a measuring device for determining the size and size distribution of particles in the nanoscopic range using scattered radiation, in particular light scattering, which permits in a simple and to an equal degree, reliable manner an independent determination of the particle density and particle size. Furthermore, an object of the present application is to determine in a simple and reliable manner, with the aide of a measuring device and using scattered radiation, the surface characteristics of sample bodies. Furthermore, an object of the present application is to be able to determine quickly and reliably the heparin portion in blood or blood serum samples, in particular heparinized blood or blood serum samples.

Accordingly, a measuring device was found to determine the size, size distribution and/or concentration of nanoscopic particles or hollow spaces in a measuring sample, the degree of opacity of such measuring samples, or the degree of roughness of surfaces, by determining the wavelength and scattering angle dependent intensities of a measurement radiation scattered on a measuring sample. An example of such a measuring device comprises a retaining device for a measuring sample to be measured, a detector comprising at least one detector inlet, an evaluation unit and at least two radiation sources which are respectively at a distance from each other and which are at a distance from the measuring sample, which comprise a multiple wavelength spectrum or a continuous spectrum, and the radiation intensities of which are adjustable and/or determinable. Via the radiation sources, one ray bundle can in each case be emitted in an essentially parallel beam in the direction of a measuring sample. The ray bundles directed onto the measuring sample, which have different radiation sources in relation to the axis between the detector inlet and the measuring sample, are aligned or can be aligned in different angles onto the measuring sample. Here, essentially parallel beams can, for example, directly leave the radiation source, or, if the radiation source does not generate directly parallel beams, such parallel beams can also be obtained indirectly, i.e., with suitable downstream auxiliary means, such as lenses. The at least two radiation sources present, which are in each case at a distance from each other and at a distance from the measuring sample, preferably have a fixed position. Here, in general, the radiation source is not changed in its position relative to an adjacent radiation source, or to adjacent radiation sources and to the measuring sample.

A measuring device as described herein may be particularly suitable for determining in a simple and reliable manner the size, size distribution and/or concentration or density of particles in the nanoscopic range which are present in a measuring sample. The measuring sample which contains these nanoscopic particles can here be viscous, fluid, or gaseous. Viscous measuring samples in the spirit of the present invention comprise, e.g., also those with semi-solid or pasty consistency. Examples of these are creams and (tooth)pastes. Furthermore, measuring samples can also be solid, non-transparent sample bodies with at least one surface which is measurable by means of scatter radiation, in particular scattered light radiation, and fixed, transparent or translucent sample bodies containing nanoscopic particles or hollow spaces. The latter sample bodies can, for example, represent glass samples containing enclosed spaces in the form of nanoscopic particles or hollow spaces. Hollow spaces can, for example, be bubble-shaped enclosed spaces such as air bubbles. In this manner, e.g., the quality of glass bodies such as lenses can be checked. As a retaining device for a viscous, fluid, or gaseous measuring sample containing a nanoscopic particle, measuring cuvettes or through-flow cells can be used, for example. The measuring device described herein is consequently suitable for both discontinuous and continuous operation.

In a particularly preferred embodiment, at least one radiation source, in particular, all radiation sources of the measuring device, the retaining device for the measuring sample or of the sample bodies, and the detector inlet are in a fixed position in relation to each other. The measuring device is thus possible to construct without any movable components, and differs in this design, for example, from a standard measuring device with a goniometer. In this manner, a structurally simple, while at the same time compact, reliable and robust construction is attainable which continuously guarantees error-free operation.

The radiation sources are preferably at an equal distance from the retaining device or from the position of the measuring sample. It is particularly preferred that the radiation sources lie on the circumference of an (imaginary) sphere or hemisphere, of a circle or a cylinder, and that they are aligned on the central point of the sphere, circle, or cylinder into which the measuring sample should advantageously be positioned. It is particularly preferred that the detector inlet is also arranged on the circumference of such a hemisphere or sphere, or on such a circle. The radiation sources, in particular also in combination with the detector or detector inlet, are preferably present on one level.

For the radiation sources, standard radiation sources can be used with which a multiple wavelength or a continuous spectrum can be generated. For example, those radiation sources are suitable which emit electromagnetic radiation in the visible range. According to a preferred embodiment, the radiation sources represent light emitting diodes, in particular, white light emitting diodes. In general, those radiation sources are possible in the spirit of the present invention which can emit electromagnetic radiation which ranges from UV radiation to close infrared radiation. Here, it is naturally sufficient when the radiation sources only cover a part of the aforementioned radiation spectrum.

In order to ensure that from one radiation source, a ray bundle with essentially parallel beams hits the measuring sample to be measured, a suitable collimating lens is, for example, arranged between the radiation source and the measuring sample. In order to focus the scattered beam on the detector inlet, a collimating lens can also be provided between the measuring sample and said detector inlet, wherein the distance from the detector inlet is determined by its focal distance. The radiation sources of the measuring devices described herein or the ray bundle which hits the measuring sample do not necessarily have to generate or comprise coherent radiation in order to be able to determine the size, size distribution and/or concentration of nanoscopic particles in measuring samples. The generation of parallel rays is already sufficient for the device.

According to a further embodiment, a radiation source, in particular all radiation sources, can also be realized via a radiation emission conductor such as a light filament cable.

Furthermore, it can be provided that the detector is a multiple wavelength detector, in particular, a grid spectrometer with diode ray or CCD detection. The detector of the measuring device is suitable for recording a plurality of scattered signals or scattered light signals which follow on from each other in time. These signals can then be analyzed and stored in the evaluation unit depending on wavelength and intensity, in particular taking into account their time succession. The detector inlet can, in one embodiment, be an integral component of the detector. In this case, the scattered radiation directly hits the detector itself. Alternatively, the detector inlet can be connected or is connectable with the detector, e.g., via at least one radiation reception conductor, for example, in the form of a light filament conductor.

The measuring device is preferably designed in such a manner that the radiation sources can be switched on and off successively. The radiation sources are accordingly preferably activated one after the other, so that preferably, only the radiation of a single radiation source constantly hits the measuring sample at any given time. The radiation pattern and the initial intensities of the individual radiation sources are either present in the evaluation unit, or are transferred directly to said unit shortly afterwards for use in an evaluation algorithm.

Here, such an embodiment is particularly preferred in which the wavelength and scattering angle dependent intensities of the radiation scattered on a measuring sample can be detected in a time-dispersed manner.

The ray bundles of radiation sources which are adjacent to each other preferably encompass an angle in the range of between 20° and 40°.

Sufficiently exhaustive results with regard to the reliable determination of size, size distribution and/or concentration of particles in measuring samples, for example, are used, in particular when working with at least four, and, in particular, with at least five radiation sources. Here it is advantageous when the radiation intensities of the radiation sources are individually adjustable. Satisfactory measuring results can however also be attained without any complication with just two radiation sources with the measuring device described herein.

The quality of the measuring device can, for example, also be increased by making the radiation intensity of a radiation source variable within a measuring cycle. If a radiation source within a measuring cycle is, for example, activated twice, i.e., it is switched on and off twice, the intensity of the radiation emitted during these two radiation processes can differ.

With the measuring device, the size, size distribution and/or the concentration of nanoscopic particles in a measuring sample, for example, with a viscous, fluid, or gaseous consistency, can simply and reliably be determined. In the spirit of the present invention, nanoscopic particles or particles in the nanoscopic range are understood to be such particles which have a size ranging from one nanometer through to the wavelength of the radiation used.

The measuring device is furthermore particularly suitable for determining the degree of opacity of fluids, in particular of processing fluids, of beer, wine, fruit juices, beer brewed from wheat or wastewater, as well as of transparent, solid measuring samples containing nanoscopic particles or hollow spaces. In general, all fluid systems can be measured which can be clouded with nanoscopic particles or floating particles.

Furthermore, the measuring device is suitable for deterring the degree of roughness or of shine of surfaces of solid sample bodies.

In a particularly preferred embodiment variant, the size, size distribution and/or quantity of carrier substances of pharmaceutical drugs can be determined with the aid of the measuring device during the course of the formulation of said pharmaceutical drugs. This aspect is not insignificant, insofar as the size and size distribution of carrier substances commonly used in the formulation of pharmaceutical drugs is essential for the effectiveness and the speed of dispensing of said pharmaceutical drugs in the organism. If, for example, an agglomeration of carrier substances occurs during the formulation of pharmaceutical drugs, as a rule, a reduced effectiveness of the intended application form of the medication is the result. The measuring device described herein may guarantee for the first time a simple, cost-efficient, and reliable check of the behaviour of carrier substances during the formulation of pharmaceutical drugs.

Furthermore, the measuring device described herein is suitable for monitoring the process during the manufacture of emulsions, suspensions, or solutions.

The measuring device can furthermore be used as a fluorometer, in particular, as a microfluorometer.

It is of particular advantage that the measuring device allows the time-dispersed determination of the size, size distribution and/or quantity or concentration of particles in a measuring sample.

An object of the present application is furthermore attained by means of a method to determine the size, size distribution and/or concentration of particles or hollow spaces in the nanoscopic range in a solid transparent or viscous or fluid or gaseous measuring sample, the degree of opacity of such measuring samples or the degree of roughness of solid surfaces of non-transparent measuring samples, comprising the following stages:

(a) provision of a measuring device according to the invention, (b) provision of a measuring sample to be measured in the retaining device for the measuring sample, (c) successive radiation of the measuring sample with at least two radiation sources, comprising the radiation of a multiple wavelength or of a continuous spectrum, with ray bundles of essentially parallel rays, (d) detection of the radiation scattered at a particular angle on the measuring sample using a detector comprising a detector inlet, and (e) wavelength and angle-dependent evaluation of the detected signal intensities of the scattered radiation in an evaluation unit in order to determine the size, size distribution and/or concentration of the nanoscopic particles present in the measuring sample, or the degree of roughness of solid surfaces.

According to a particularly preferred embodiment of the method, it is provided that at least two, in particular, a plurality of wavelength and angle-dependent intensities of the scattered radiation are recorded of at least two radiation sources which are in a fixed position for one measuring procedure, one after the other, and in particular, at short time intervals, so that a time-dispersed measurement of the scattered radiation can be realized. A plurality of wavelength and angle-dependent intensities in the spirit of the present invention are obtained for example by recording the intensities of at least ten wavelengths when at least two, and, in particular, at least four or five, radiation sources are used.

In general, angle-dependent intensity measurements when at least two, and, in particular, at least four or five radiation sources are used is sufficient for approximately ten to 256 wavelengths, in order to be able to make the desired statements regarding the size, distribution or concentration of nanoscopic particles or hollow spaces in measuring samples. Naturally, time-dispersed measurements are also possible, in which the intensities of over 256 wavelengths are measured depending on the scattering angle.

In general, the method according to the present invention can be used for a measuring cycle of up to approximately 4,000 wavelength measuring points. The method thus allows the 3-value matrix characteristic for a measuring sample at a specific point in time, consisting of evaluation points for the scattering angle/wavelength/intensity parameters.

Thus, it is possible in the evaluation unit to record a plurality of signals or signal patterns occurring in one after the other in time, and to store and analyze them, in particular, taking into account this time sequence. Brief time intervals in the spirit of the present invention comprise, for example, intervals ranging from micro or milliseconds to seconds. As a result, a plurality of signals can be recorded in each case in intervals of micro or milliseconds to seconds. The intervals between the individual measurements can vary within a measurement series, or be kept constant. The intervals between intensity measurements of the scattering radiation which follow on from each other and which are angle and wavelength dependent can thus be selected to be so brief that changes to the particles, e.g., to the size, distribution, or concentration can easily be monitored over the period of time. For example, every ten milliseconds, an angle and wavelength dependent intensity measurement of the radiation scattered on the measuring sample can be undertaken.

Advantageously, in at least one embodiment, the wavelength-dependent intensities are recorded in succession under different scattering angles. For this purpose, different radiation sources are, for example, switched on and off one after the other. The radiation sources, which are preferably, but not necessarily, radiation sources which are adjacent to each other, are here successively shut down, so that a specific scattering angle can be assigned to each radiation from a specific radiation source due to the position of said source relative to the measuring sample. The intensity of the outgoing radiation of a radiation source is also known or can be determined. A time-dispersed measurement can therefore be achieved by detecting or monitoring dependent on the scattering angle the wavelength-dependent intensity at shorter intervals, i.e., faster than the progress of change in the detected particles.

The method described herein uses, in particular, the circumstance that the radiation sources of the measuring device can be switched on and off successively according to a specified pattern. Adjacent radiation sources are preferably switched on and off one after the other, respectively. In general, however, the sequence of the on-off switching procedures can be freely selected for the radiation sources present in a measuring device, e.g., they can also be completely or partially repeated, and optimally attuned accordingly to the respective analysis problem.

Accordingly, it is of particular advantage when at least two, in particular adjacent, radiation sources are switched on and off simultaneously or one after the other. A further development is furthermore characterized by the fact that at least one radiation source is switched on and off in pulses, and that at least one further radiation source, in particular all other radiation sources, radiate continuously during the measuring procedure. Of particular advantage here is a procedure in which at least two, in particular, all radiation sources are switched on and off in pulses either synchronously or asynchronously.

It has been shown to be particularly advantageous to use only those scattered signals or scattered light signals for the evaluation which are obtained when only one radiation source is switched on. Scattered signals or scattered light signals which are obtained during overlapping on and off switching procedures or two or more radiation sources are preferably to be disregarded for the determination of the size, size distribution and/or quantity of particles in a measuring sample, or of the roughness of the surface of a solid sample body. Accordingly, the measuring sample is in this mode not radiated simultaneously with two or more radiation sources, in order to thus secure scattered signals or scattered light signals which can be optimally evaluated.

With the method described above, and with the measuring device described herein, wavelength and angle-dependent intensities can thus be recorded, stored, and evaluated from radiation scattered on a measuring sample. Here, with the aid of known scatter theories for particles, such as Mie scattering, Rayleigh scattering, or Rayleigh-Gans-Debye scattering, for example, an adaptation of the parameters of these scattering theories to the radius of the scattering particles or to their refractive index can be made, for example, using the least-square method.

According to one embodiment, in the framework of a qualitative or semi-qualitative evaluation, the wavelength and angle-dependent intensity of scattered radiation can be recorded and then stored as a function of these two variables in the form of a characteristic curve field. An absolute calibration can then follow this using measuring samples with a known concentration and particle size. Finally, a gradient analysis can be used to determine the change in scattering center density and size. Here, the characteristic curve represents a constant and clear function.

In the field of surgery, such as heart surgery, or with other surgical operations, such as, transplants, the clotting of the blood during the operation is significantly reduced with the aid of heparin, which is applied intravenously, so that "heparinized" blood is present in the organism. For this purpose, non-fractionated, high-molecular heparin is usually used. The dosage of the heparin is generally calculated empirically depending on the body weight of the patient (approx. 1.5 to 1.8 mm/kg). The heparin quantities calculated in this manner do not generally represent a heparin dosage which is optimally adjusted to the individual circumstances.

Currently, the quantity of heparin present in the blood is therefore monitored during the operation with the aid of ACT tests (activated clotting time). A method of this type is described, e.g., in EP 1 221 620 A1. Here, through the administration of suitable anti-coagulants such as Factor Xa, the time duration until the blood clots is determined. This method requires relatively large quantities of blood samples, but is still always relatively imprecise and also very time-intensive. After the completion of the operation, for example, a bypass operation, the heparin which has been applied and which is still effective must be neutralized, which is usually achieved by administering protamine. If this quantity of heparin is incorrect or has been calculated too imprecisely, problems may occur in connection with the dosage of a suitable protamine quantity. For example, with an under dose of protamine, internal bleeding may arise, while with an overdose of protamine, post-operative coagulation is a possibility.

According to a further aspect of the present invention described herein, a method for determining the heparin share is therefore also provided, in particular, in heparinized blood or blood serum samples, comprising the following stages:

(a) provision of a measuring device according to the invention, (b) provision of a blood or blood serum sample, in particular, one which is heparinized, which has already been mixed with at least one heparin antagonist and/or which, when present in the retaining device, is mixed with at least one heparin antagonist in order to form an antagonist/heparin complex, (c) successive radiation with at least two radiation sources, comprising the radiation of a multiple wavelength or of a continuous spectrum, with ray bundles of essentially parallel rays, (d) detection of the radiation scattered at a particular angle on the measuring sample using a detector comprising a detector inlet, and (e) wavelength and angle-dependent evaluation of the detected signal intensities in an evaluation unit in order to determine the concentration of the antagonist/heparin complex present in the measuring sample.

The at least two radiation sources present, which are respectively at a distance from each other and at a distance from the measuring sample, preferably have a fixed position. Here, in general, the radiation source is not changed during measurement in its position relative to an adjacent radiation source, or to adjacent radiation sources, or relative to the measuring sample. The calculation of the heparin content is particularly advantageously realized when at least two, in particular adjacent, radiation sources are switched on and off simultaneously or one after the other, respectively. Here, it can, in particular, be provided that the radiation sources are switched on and off successively according to a specified pattern.

A further development of this method furthermore provides that at least one radiation source is switched on and off in pulses, and that at least one further radiation source, in particular, all other radiation sources, radiate continuously during the measuring procedure. Here, according to a further embodiment, it is furthermore of advantage that at least two, in particular all, radiation sources are switched on and off synchronously or asynchronously in pulses. Here, it is of particular advantage when for the evaluation, only those scattered light signals are used which are obtained when only one radiation source is switched on. A preferred method variant is finally characterized by the fact that two or more radiation sources do not radiate on the measuring sample simultaneously in order to obtain scattered light signals which can be evaluated.

According to a particularly preferred embodiment of the method, it is provided that at least two, in particular a plurality, of wavelength and angle-dependent intensities of the scattered radiation from one or at least two radiation sources are recorded one after the other, in particular, at brief time intervals, so that a time-dispersed measurement of the scattered radiation can be conducted. The information given above regarding the time-dispersed measurement also applies here accordingly.

With the method to determine the heparin share in heparinized blood or blood serum samples, for example, a fast and precise method for determining the heparin level is provided. In particular, levels for patients with increased heparin sensitivity can be very precisely set.

As an antagonist, an alkaline protein is preferably used, in particular, protamine. It has been shown to be particularly advantageous to add the antagonist in excess in relation to the quantity of heparin present in the measuring sample. With this method, the heparin content can be precisely calculated by determining, in particular, dispersed over time, the opacity of the blood sample or the blood serum sample.

DESCRIPTION OF THE DRAWINGS

Further details and advantages of the present invention will now be explained in greater detail with reference to the following drawings, in which.

DETAILED DESCRIPTION

Figure 1:
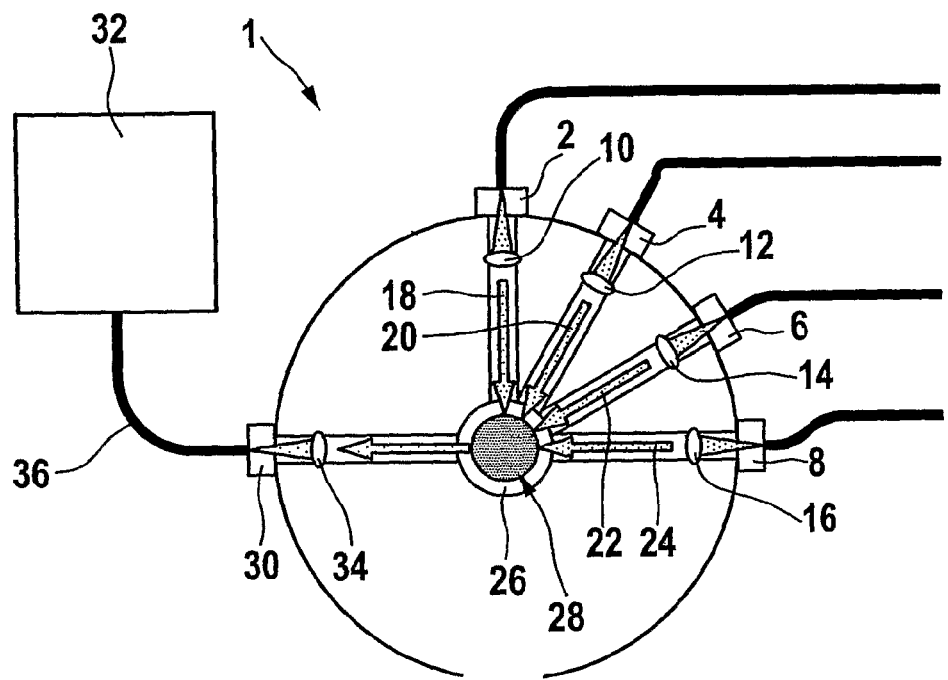
FIG. 1 shows a schematic view of one embodiment of a measuring device according to the invention.

FIG. 1 shows a measuring device which comprises four radiation sources 2, 4, 6, and 8, which are arranged at a distance from each other, and which radiate respectively one multiple wavelength spectrum, in particular, a continuous spectrum. With the embodiment shown, the radiation sources 2, 4, 6, and 8 and the recording unit lie at one level and are arranged along a circle circumference. In the area of the central point of the circle, the sample retaining device 26 is attached. Transmission and receiver radiation paths run radially in relation to this circle.

In order to obtain parallel or nearly parallel rays, a collimator lens 10, 12, 14, and 16 is switched downstream of each radiation or light source. The parallel rays 18, 20, 22, and 24 which are generated are as far as possible all aligned to sample 28 which is arranged in the central point of the (imaginary) circle in a measuring cuvette 26. The sample 28 can, for example, represent opaque beer brewed from wheat or waste water containing floating particles.

The radiation sources 2, 4, 6, and 8, as is the recording unit 30, and the sample retaining device 26, are arranged in an unmovable position in relation to each other. The parallel light rays of adjacent radiation sources enclose a constant angle. In the present case, the angle between adjacent ray bundles is in each case 30°. In relation to the axis which runs through the detector 30 and the sample retaining chamber 26, the respective ray bundles stand accordingly at an angle of 0°, 30°, 60°, and 90°. Via the collimator lens 34, radiation scattered in the direction of the recording unit 30 is coupled into a light conductor 36 and guided to a detector 32. This can, for example, be a CCD detector which detects the intensity of the radiation which hits the sample, depending on the wavelength.

The particles present in the measuring sample in the sample retaining chamber 26 are according to one embodiment measured in such a manner that the radiation sources 2, 4, 6, and 8 are switched on and off one after the other. In this way, a data record of wavelength and angle-dependent intensities can be obtained in only a few seconds of measuring time through a combination of different angles, which represents the scattering behavior of the particles to be analyzed, using the entire emission spectrum of the individual radiators. These radiators can, for example, be white light emitting diodes. In this way, a time-dispersed determination of the intensity of the scattered radiation depending on the scattering angle and the wavelength is achieved using the entire emission spectrum of a radiator. The data record obtained can in a simple manner also be standardized, e.g., to an absolute particle size which is determined via analytical ultra-centrifugation.

Figure 2:
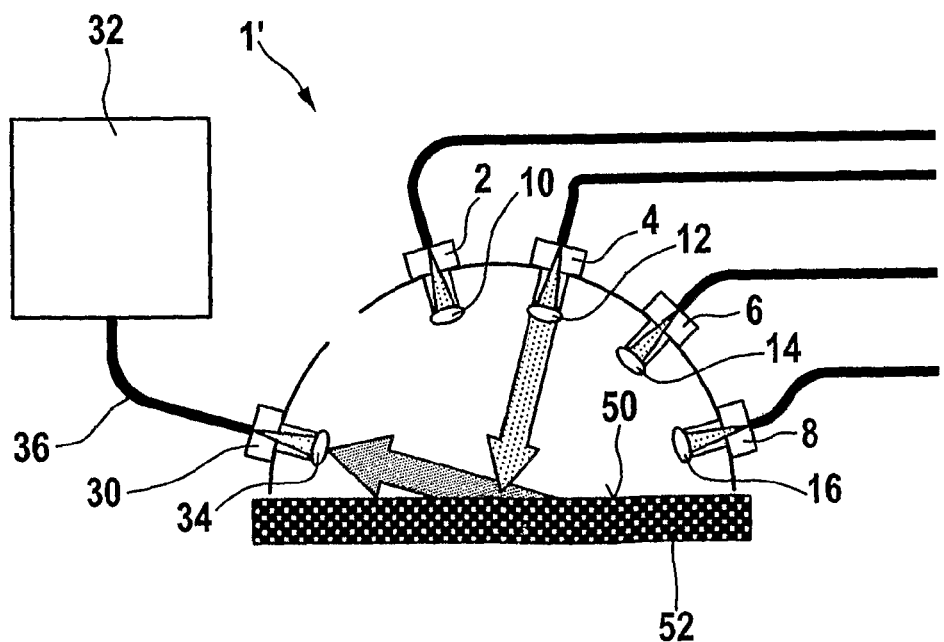
FIG. 2 shows a schematic view of an alternative embodiment of a measuring device according to the invention.

FIG. 2 gives an alternative embodiment of a measuring device according to the invention 1'. In contrast to the measuring device shown in FIG. 1, with the present measuring device, it is not a measuring fluid contained in a sample retaining chamber which is measured, but the surface 50 of a solid sample body 52. As with the device shown in FIG. 1, the radiation sources 2, 4, 6, and 8 are arranged on the circumference of a circle, and are aligned to the central point of said circle, where at least one section of the surface 50 of the sample body 52 to be measured is located. In turn, it is ensured by using collimators 10, 12, 14, and 16 that an essentially parallel radiation hits the sample surface 50. The detector unit 30 also has a collimator 34 and is also arranged on the circumference of the aforementioned circle. The radiation sources 2, 4, 6, and 8 are arranged in such a manner that the ray bundles which they emit enclose an angle of 120°, 190°, 60°, or 30° with the sample surface. The detection unit 30 is arranged on the circumference of the (imaginary) circle in such a manner that scattered radiation is recorded which is scattered in the central point of the circle at an angle of 30° in relation to the sample surface. The detection and evaluation are essentially conducted in the same way as for the measuring device shown in FIG. 1. With the measuring device described in FIG. 2, the surface roughness, coloration, or shine of sample surfaces can be determined in a simple manner.

The features of the invention disclosed in the above description, in the claims and in the drawings can be implemented for the realization of the invention in its different embodiments either individually or in any combination required.

LIST OF REFERENCE NUMERALS

2 Light source
4 Light source
6 Light source
8 Light source
10 Collimator lens
12 Collimator lens
14 Collimator lens
16 Collimator lens
18 Parallel light rays
20 Parallel light rays
22 Parallel light rays
24 Parallel light rays 26 Sample retaining device
28 Sample
30 Recording device
32 Detector
34 Collimator lens
36 Light conductor
50 Surface
52 Sample body

What is claimed is:

1. A measuring device for determining the size, size distribution, and/or concentration of nanoscopic particles or hollow spaces in a measuring sample, the degree of opacity of such a measuring sample, or the degree of roughness of a surface of the measuring sample, by determining the wavelength and scattering angle-dependent intensities of a measuring radiation scattered from the measuring sample, the measuring device comprising:
   a retaining device for a measuring sample to be measured;
   a detector, comprising at least one detector inlet;
   an evaluation unit; and
   at least two radiation sources that are respectively arranged at a distance from each other and at a distance from the measuring sample, which radiation sources provide radiation of a multiple wavelength spectrum or a continuous spectrum, and the radiation intensities of which can be adjusted and/or determined, wherein the radiation sources are in each case configured to emit a ray bundle in essentially parallel rays in the direction of the measuring sample, and wherein the ray bundles that are directed from different radiation sources onto the measuring sample are aligned at different angles onto the measuring sample, in relation to the axis between the detector inlet and the measuring sample;
   wherein the measuring sample represents a viscous fluid or gaseous measuring sample that contains nanoscopic particles, or a solid, transparent sample body containing nanoscopic particles or hollow spaces that are measurable from the scattered radiation.

2. The measuring device according to claim 1, wherein the retaining device for the viscous fluid or gaseous measuring sample comprises a measuring cuvette or a through-flow cell.

3. The measuring device according to claim 1, wherein at least one radiation source, the retaining device for the measuring sample or the sample body and the detector inlet are all in a fixed position in relation to each other.

4. The measuring device according to claim 1, wherein the radiation source comprises a light emitting diode.

5. The measuring device according to claim 1, wherein at least one radiation source, via which a ray bundle can be emitted in essentially parallel rays, comprises a light conductor.

6. The measuring device according to claim 1, further comprising at least one collimator lens arranged between the radiation source and the measuring sample and/or between the measuring sample and the detector inlet, so that said collimator lens can be passed by the radiation emitted from the radiation source prior to hitting the measuring sample, or by the scattered radiation prior to hitting the detector inlet.

7. The measuring device according to claim 1, wherein the detector represents a multiple wavelength detector.

8. The measuring device according to claim 1, wherein the radiation sources are configured to switch on and off successively.

9. The measuring device according to claim 1, wherein the detector is configured to detect the wavelength and scattering angle-dependent intensities of the radiation scattered from the measuring sample in a time-dispersed manner.

10. The measuring device according to claim 1, wherein the radiation sources are positioned approximately the same distance from the measuring sample to be measured.

11. The measuring device according to claim 1, wherein the ray bundles of adjacent radiation sources enclose an angle in the range of approximately 20 to 40°.

12. The measuring device according to claim 1, comprising in total at least four radiation sources.

13. The measuring device according to claim 1, wherein the radiation sources are configured such that the radiation intensities of the radiation sources can be set individually.

14. The measuring device according to claim 1, wherein the radiation intensity of a radiation source is variable within a measuring cycle.

15. The measuring device according to claim 1, wherein the detector inlet is connectable or connected to the detector via at least one radiation reception conductor.

16. A method for determining the size and/or concentration of particles or hollow spaces in the nanoscopic range in a solid, transparent or viscous or fluid or gaseous measuring sample, of the degree of opacity in said measuring sample or of the degree of roughness of a solid surface of a non-transparent measuring sample, comprising:
   (a) providing a measuring device according to claim 1;
   (b) providing a measuring sample to be measured in the retaining device for the measuring sample;
   (c) radiating the measuring sample with radiation from at least two radiation sources that emit radiation of a multiple wavelength or of a continuous spectrum, with ray bundles of essentially parallel rays;
   (d) detecting the radiation scattered at a particular angle from the measuring sample using a detector comprising a detector inlet; and
   (e) evaluating the wavelength and angle-dependent characteristics of the signal intensities of the detected scattered radiation to determine the size, size distribution and/or concentration of the nanoscopic particles present in the measuring sample.

17. The method according to claim 16, wherein a plurality of wavelength and angle-dependent intensities of the scattered radiation of at least two radiation sources are recorded one after the other at brief time intervals to obtain a time-dispersed measurement of the scattered radiation.

18. The method according to claim 16, wherein at least two adjacent radiation sources are switched on and off simultaneously.

19. The method according to claim 16, wherein the radiation sources are successively switched on and off according to a specified pattern.

20. The method according to claim 16, wherein at least one radiation source is switched on and off in pulses, and at least one further radiation source radiates continuously during the measuring procedure.

21. The method according to claim 16, wherein at least two radiation sources are switched synchronously on and off in pulses.

22. The method according to claim 16, wherein said evaluating uses only the detected scattered radiation signals that are obtained when only one radiation source is switched on.

23. The method according to claim 16, wherein two or more radiation sources do not radiate the measuring sample simultaneously, in order to obtain scattered radiation signals which can be evaluated.

24. The method according to claim 16, wherein the measuring sample comprises a viscous fluid or gaseous or nanoscopic particle, a solid, transparent sample body containing nanoscopic particles or hollow spaces, or a solid, non-transparent sample body with at least one surface that is measurable using scattered radiation.

25. A method to determine the heparin share in blood samples or blood serum samples, comprising:
(a) providing a measuring device that includes:
a retaining device for a measuring sample to be measured;
a detector comprising at least one detector inlet;
an evaluation unit; and
at least two radiation sources that are respectively arranged at a distance from each other and at a distance from the measuring sample, which radiation sources provide radiation of a multiple wavelength spectrum or a continuous spectrum, and the radiation intensities of which can be adjusted and/or determined, wherein the radiation sources are in each case configured to emit a ray bundle in essentially parallel rays in the direction of the measuring sample, and wherein the ray bundles that are directed from different radiation sources onto the measuring sample are aligned at different angles onto the measuring sample, in relation to the axis between the detector inlet and the measuring sample;
(b) providing a blood sample or blood serum sample in the retaining device for the measuring sample, which is already mixed with at least one heparin antagonist and/or which when present in the retaining device is mixed with at least one heparin antagonist to form an antagonist/heparin complex;
(c) radiating the measuring sample with radiation from the at least two radiation sources that emit radiation of a multiple wavelength or of a continuous spectrum, with ray bundles of essentially parallel rays;
(d) detecting the radiation scattered at a particular angle from the measuring sample using the detector; and
(e) evaluating the wavelength and angle-dependent characteristics of the signal intensities of the detected scattered radiation to determine the concentration of the antagonist/heparin complex present in the measuring sample.

26. The method according to claim 25, wherein the antagonist comprises an alkaline protein.

27. The method according to claim 25, wherein the antagonist is added in excess in relation to the quantity of heparin present in the measuring sample.

28. The method according to claim 25, wherein the heparin content is determined via a time-dispersed determination of the opacity of the blood sample or blood serum sample.

29. The method according to claim 25, wherein at least two adjacent radiation sources are switched on and off simultaneously.

30. The method according to claim 25, wherein the radiation sources are successively switched on and off according to a specified pattern.

31. The method according to claim 25, wherein at least one radiation source is switched on and off in pulses, and at least one further radiation source radiates continuously during the measuring procedure.

32. The method according to claim 25, wherein at least two radiation sources are switched on and off synchronously or asynchronously in pulses.

33. The method according to claim 25, wherein said evaluating uses only the detected scattered radiation signals that are obtained when only one radiation source is switched on.

34. The method according to any one claim 25, wherein two or more radiation sources do not radiate the measuring sample simultaneously, in order to obtain scattered radiation signals which can be evaluated.

35. The method according to claim 25, wherein a plurality of wavelength and angle-dependent intensities of the scattered radiation of at least two radiation sources are recorded one after the other at brief time intervals to obtain a time-dispersed measurement of the scattered radiation.

36. The measuring device according to claim 4, wherein the light emitting diode is a white light emitting diode.

37. The measuring device according to claim 7, wherein the multiple wavelength detector is a grid spectrometer with diode array or CCD detection.

38. The measuring device according to claim 1, comprising in total at least five radiation sources.

39. The method according to claim 16, wherein at least two adjacent radiation sources are switched on and off one after the other respectively.

40. The method according to claim 16, wherein at least one radiation source is switched on and off in pulses, and all other radiation sources radiate continuously during the measuring procedure.

41. The method according to claim 16, wherein at least two radiation sources are switched asynchronously on and off in pulses.

42. The method according to claim 16, wherein all radiation sources are switched synchronously or asynchronously on and off in pulses.

43. The method according to claim 26, wherein the alkaline protein is protamine.

44. The method according to claim 25, wherein at least two adjacent radiation sources are switched on and off one after the other respectively.

45. The method according to claim 25, wherein at least one radiation source is switched on and off in pulses, and all other radiation sources radiate continuously during the measuring procedure.

46. The method according to claim 25, wherein all radiation sources are switched on and off synchronously or asynchronously in pulses.

* * * * *